United States Patent [19]

Sahatjian et al.

[11] Patent Number: 5,238,004
[45] Date of Patent: Aug. 24, 1993

[54] HIGH ELONGATION LINEAR ELASTIC GUIDEWIRE

[75] Inventors: Ronald Sahatjian, Lexington; Fernando Alvarez de Toledo, Concord, both of Mass.

[73] Assignee: Boston Scientific Corporation, Watertown, Mass.

[21] Appl. No.: 954,469

[22] Filed: Sep. 30, 1992

Related U.S. Application Data

[63] Continuation of Ser. No. 507,375, Apr. 10, 1990, abandoned.

[51] Int. Cl.⁵ .............................................. A61B 5/00
[52] U.S. Cl. ................................... 128/772; 128/657; 604/195
[58] Field of Search ................... 128/657, 658, 772; 604/90, 95, 281

[56] References Cited

U.S. PATENT DOCUMENTS

| | | |
|---|---|---|
| 3,174,851 | 3/1965 | Buehler et al. |
| 3,351,463 | 11/1967 | Rozner et al. |
| 3,558,369 | 1/1971 | Wang et al. |
| 3,618,613 | 11/1971 | Schulte |
| 3,620,212 | 11/1971 | Fannon et al. |
| 3,740,839 | 6/1973 | Otte et al. |
| 3,753,700 | 8/1973 | Harrison et al. |
| 3,757,768 | 9/1973 | Kline |
| 3,786,806 | 1/1974 | Johnson et al. |
| 3,789,841 | 2/1974 | Antoshkiw |
| 3,832,243 | 8/1974 | Donkersloot et al. |
| 3,890,977 | 6/1975 | Wilson |
| 4,019,925 | 4/1977 | Nenno et al. |
| 4,035,007 | 7/1977 | Harrison et al. |
| 4,037,324 | 7/1977 | Andreasen |
| 4,144,057 | 3/1979 | Melton et al. |
| 4,148,635 | 4/1979 | Smith, Jr. |
| 4,170,990 | 10/1979 | Baumgart et al. |
| 4,198,081 | 4/1980 | Harrison et al. |
| 4,205,293 | 5/1980 | Melton et al. |
| 4,233,690 | 11/1980 | Akins |
| 4,274,872 | 6/1981 | Melton et al. |
| 4,310,354 | 1/1982 | Fountain et al. |
| 4,398,969 | 8/1983 | Melton et al. |
| 4,407,776 | 10/1983 | Suzuki |
| 4,411,655 | 10/1983 | Schreck |
| 4,427,000 | 1/1984 | Ueda |
| 4,430,081 | 2/1984 | Timmermans |
| 4,439,197 | 3/1984 | Honda et al. |
| 4,449,518 | 5/1984 | Konomura et al. |

(List continued on next page.)

FOREIGN PATENT DOCUMENTS

| | | |
|---|---|---|
| 1232814 | 2/1988 | Canada |
| 0141006 | 5/1985 | European Pat. Off. |
| 1599564 | 7/1970 | France |
| 2401668 | 4/1979 | France |
| 57-63655 | 12/1982 | Japan |
| 60-63066 | 3/1985 | Japan |
| 62-47445 | 9/1987 | Japan |
| 1-124473 | 5/1989 | Japan |
| 1-170474 | 7/1989 | Japan |
| 8804940 | 7/1988 | World Int. Prop. O. |

OTHER PUBLICATIONS

Terumo, English translation of Japanese Patent No. 170475/89.

Bensmann et al.; Anwendungen des Memory-Effektes in der Medizin; *Pulvermetallurgie Renner*, 35:312–318; Apr. 1981.

Bensmann et al.; Untersuchungen der Memory-Legierung Nickel-Tital und Überlegungen zu ihrer Anwendung im Bereich der Medizin; *Tech. Mitt. Krupp*; 37:21–33; (1979).

*Primary Examiner*—Max Hindenburg
*Attorney, Agent, or Firm*—Fish & Richardson

[57] ABSTRACT

A guidewire and a method for its manufacture, wherein at least the distal portion of the guidewire comprises an element made of a precursor of a superelastic alloy such as a Ni—Ti linear elastic alloy. The element exhibits a stress strain curve with a linear stress-strain relationship and a yield point. At room temperature to body temperature the precursor is in the martensitic phase. The distal portion of the guidewire is deformable beyond the yield point by the physician in the field to a desired set shape and exhibits resistance to kinking during insertion into the body as a result of its elasticity.

27 Claims, 4 Drawing Sheets

U.S. PATENT DOCUMENTS

| | | |
|---|---|---|
| 4,450,686 | 5/1984 | Banks . |
| 4,472,213 | 9/1984 | Tabei et al. . |
| 4,490,112 | 12/1984 | Tanaka et al. . |
| 4,503,569 | 3/1985 | Dotter . |
| 4,505,767 | 3/1985 | Quin . |
| 4,507,115 | 3/1985 | Kambara et al. . |
| 4,509,517 | 4/1985 | Zibelin . |
| 4,512,338 | 4/1985 | Balko et al. . |
| 4,554,929 | 11/1985 | Samson et al. . |
| 4,586,969 | 5/1986 | Tamura et al. . |
| 4,601,283 | 7/1986 | Chikama . |
| 4,616,656 | 10/1986 | Nicholson et al. . |
| 4,631,094 | 12/1986 | Simpson et al. . |
| 4,634,477 | 1/1987 | Sugimoto et al. . |
| 4,637,962 | 1/1987 | Albrecht et al. . |
| 4,657,822 | 4/1987 | Goldstein . |
| 4,664,627 | 5/1987 | Kyotani et al. . |
| 4,665,906 | 5/1987 | Jervis . |
| 4,770,725 | 9/1988 | Simpson et al. . |
| 4,925,445 | 3/1990 | Sakamoto et al. ............... 604/95 |

Golestaneh; Energetic Shape Recovery Associated With Martensitic Transformation in Shape-Memory Alloys; *Acta Metallurgica*; 28:1427–36; (1930).

Johnson; Thermomechanical Characteristics of Nitinol; Thesis; Naval Postgraduate School, Monterey, Calif.; (Mar. 1975).

Melton et al.; The Mechanical Properties of NiTi--Based Shape Memory Alloys; Acta Metallurgica 29:393–398; (1981).

Mendelson; (Perkins, ed.) Mechanisms for Martensite Formation and the Shape Memory Effect; *Shape Memory Effects im Alloys* (1975).

Miura et al.; (Perkins, ed.) Superelasticity and Shape Memory Effect in Cu–Sn Alloys; *Shape Memory Effects in Alloys*; (1975).

NTIS Tech. Note; Properties for Nickel/Titanium Wire and Tubing: Data on two useful forms of shape--memory alloy are presented; U.S. Dept. of Energy; (Apr. 1984).

Schetky (Kirk–Othmer, ed.) Shape–Memory Alloys; *Encylopedia of Chemical Technology*; 20; 726–36 (1982).

Schetky; Shape-Memory Alloys; *Scientific American*; pp. 74–82; (Nov., 1979).

Suzuki; Shape Memory and Super–elasticity Effects in NiTi Alloys; 30:185–92.

Winkler et al.; Konstruieren mit superplastisch umgeformten Blechbauteilen in der Luft–und Raumfahrt; *Konstruieren Mit Blech; VDI Berichte 523; (Nov., 1984)*.

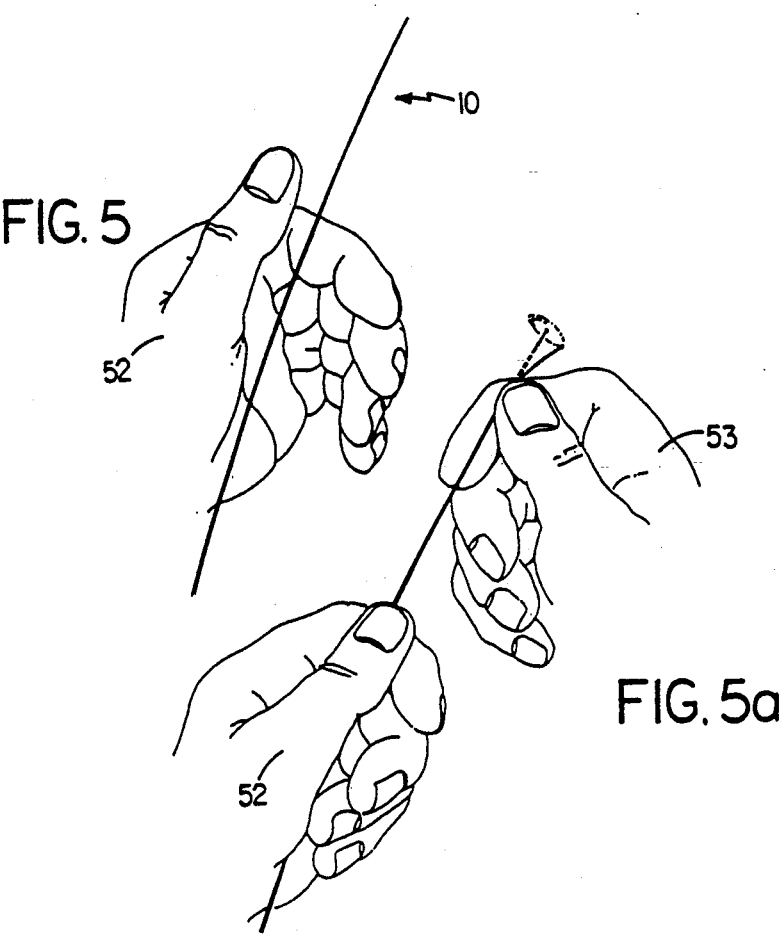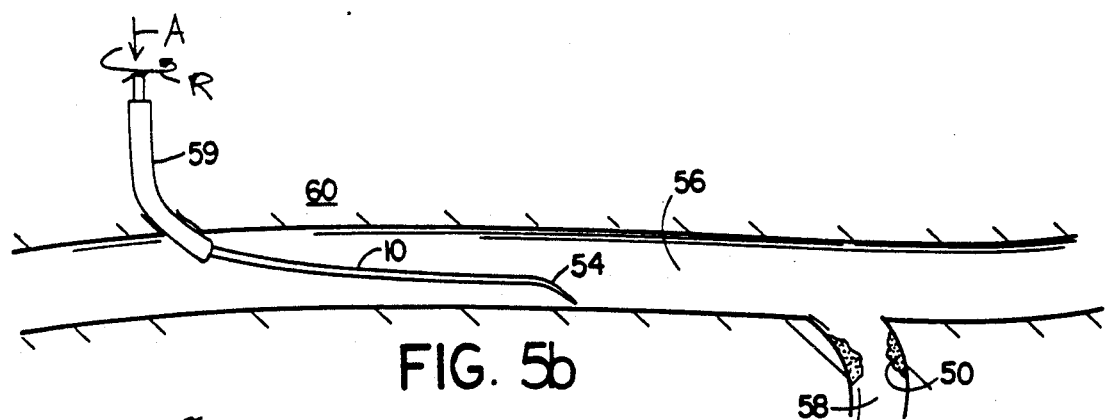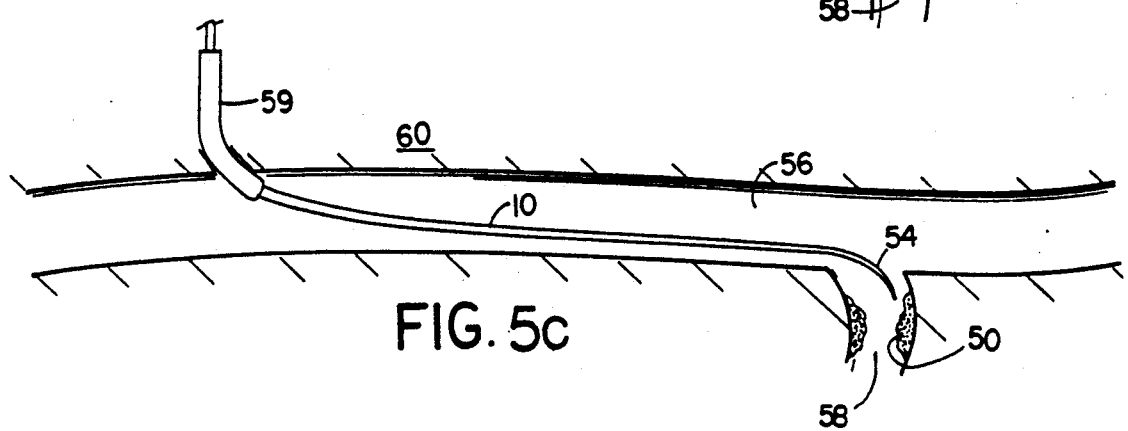

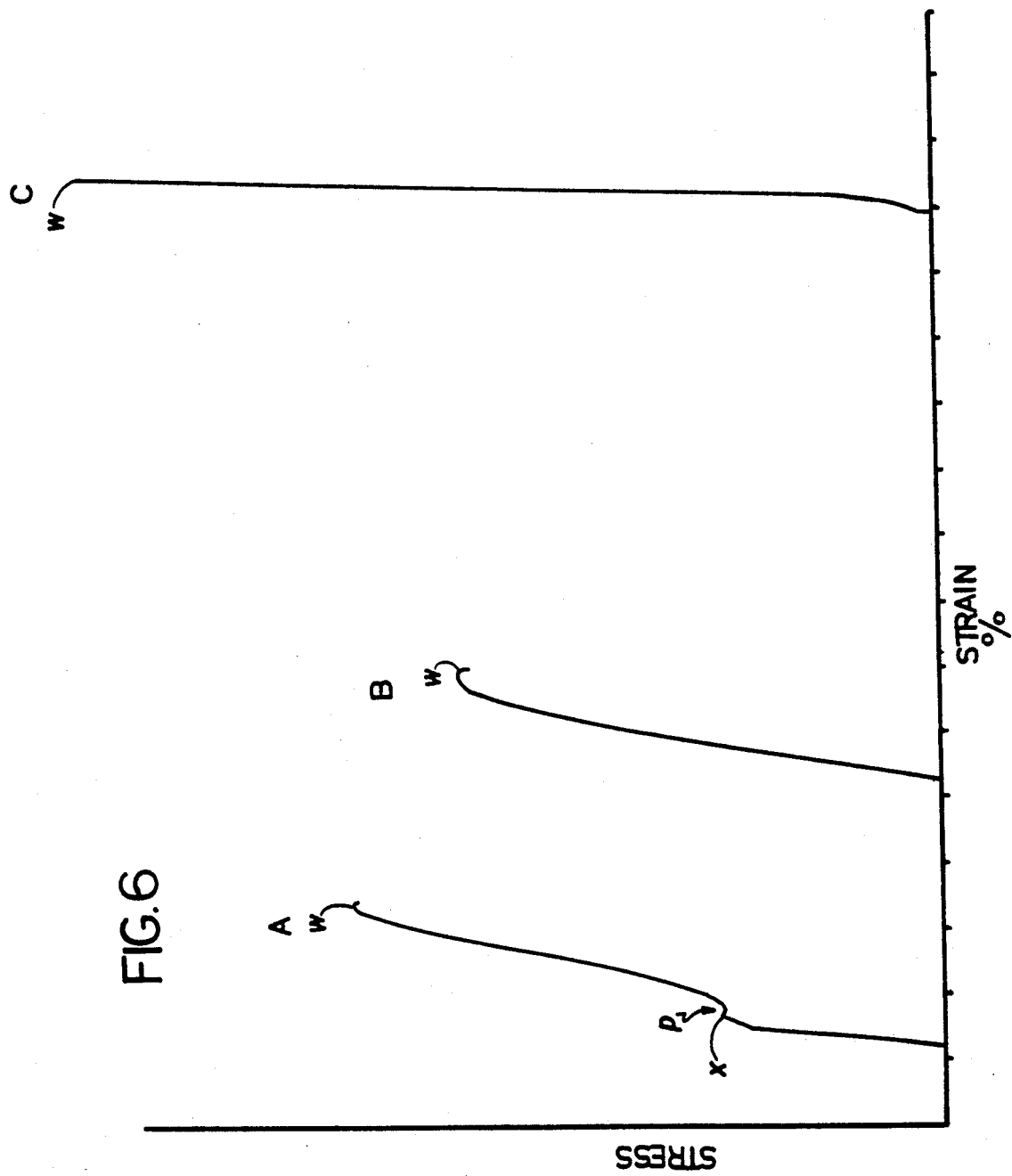

HIGH ELONGATION LINEAR ELASTIC GUIDEWIRE

This is a continuation of application Ser. No. 07/507,375, filed Apr. 10, 1990, now abandoned.

FIELD OF THE INVENTION

This invention relates to guidewires for navigating internal passageways of a body.

BACKGROUND OF THE INVENTION

Generally, the distal end of a guidewire is introduced into a body by a physician, e.g., through a puncture opening. The physician manipulates the tip of the guidewire through tortuous aspects of the body's passageways to a site to be treated. A catheter or other medical device is advanced over the guidewire to the treatment site and the guidewire is then removed, leaving the catheter in place.

In order for the physician to have maximal control over the guidewire, and to ensure the patient's safety, it is important that the guidewire be as small in diameter as possible, particularly in the tip region, but not so small as to create a danger of the tip breaking loose in the body. It is also important that the guidewire be smooth to allow ready advancement and retraction within the passageways; that the distal tip of the guidewire be highly flexible to permit negotiation of difficult turns within the body; that the guidewire be stiff enough axially to be advanced by thrust from the proximal end outside the body without kinking, i.e., turning back upon itself; and that the guidewire have good steerability or torque response. Most prior art guidewires compromise these desired features.

To aid the steering of the element into a desired lumen, it is common to give at least the tip portion of the element a predetermined curvature that complements the lumen path. Many guidewires available today have a curvature formed in the factory during manufacture. Some guidewires made of conventional materials, e.g., stainless steel, can be tip-formed by the physician prior to insertion, a feature found desirable by many.

Fuji Terumo Co. Ltd., EPA 0 141 006 describes a guidewire having at least portions of the body and/or flexible distal end formed of a superelastic metal member, e.g., a specially heat treated Ti—Ni alloy (Nitinol). The end may have a curved tip to aid steering. Because of the high elongation of the superelastic materials, a guidewire which has been previously curvedly deformed can be straightened when being introduced to the body through a needle and then will restore itself to the original curved shape when inserted in a blood vessel (p. 15).

In WO 88/094940, also by Terumo, a guidewire is formed by differentially heat treating a linear material, e.g., an elastic alloy such as an ultra elastic alloy (e.g., Ni—Ti) so that the flexibility increases progressively from the base to the tip.

SUMMARY OF THE INVENTION

Generally, the invention features a guidewire, preferably an angiographic guidewire, a method for its manufacture, and a method for its use.

In one aspect, the invention features a guidewire device having a distal portion comprised of a precursor of a superelastic alloy. The distal portion has a stress-strain curve exhibiting a yield point without passing through a substantial plateau. The distal portion of the guidewire is deformable beyond the yield point to a desired set shape.

In various aspects of the guidewire device, the precursor is in the martensite phase at room temperature to body temperature; the precursor is selected from the group consisting of an alloy of In—Tl, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn; preferably the alloy is selected from the group consisting of Ni—Ti, Cu—Al—Ni and Cu—Zn—Al; more preferably, the precursor is an alloy of about 55%/45% Ni—Ti; at least part of the distal portion is smaller than an integral portion of the guidewire proximal thereof which is also comprised of the precursor of a superelastic alloy; at least part of the portion formed of the precursor is tapered; the guidewire includes a core element comprised of the precursor, the core element extending proximally, integrally from the element of the distal portion; the guidewire includes a polymeric coating; the coating is polytetrafluoroethylene; the coating is a lubricious polymer; the coating includes an antithrombogenic agent; the agent is heparin; the distal portion has an element comprised of the precursor of a superelastic alloy and further a flexible spring coil surrounds the element; the spring coil is more flexible than the element; the guidewire may be in the form of an angiographic guidewire having a total length of about 145 cm, or a gastrointestinal (GI) guidewire with a total length of about 450 cm, either of which may have a body portion of about 0.020 to 0.290 inch diameter, a taper portion about 7 to 10 cm long and a tip portion about 2 to 10 cm long with a diameter of about 0.007 inch.

In another aspect, the invention features a method of forming a guidewire device by providing an element comprised of a precursor of a superelastic alloy, the element having a linear stress strain curve exhibiting a yield point, without passing through a substantial plateau and reducing the diameter of at least a portion of the element under conditions avoiding substantial heating. Thereafter, the element is incorporated into a guidewire device, with the reduced diameter portion forming part of the distal portion of the guidewire device. The distal portion is elastically flexible while being capable of being given a desired permanent set by manual stressing of the distal region beyond its yield point.

In various aspects of the method, the element is selected from In—Tl, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn; preferably the element is 55%/45% Ni—Ti; the method further includes selecting an element in the martensite phase at room temperature to body temperature and maintaining the martensite phase during the formation of the guidewire; the maintaining includes maintaining the temperature of the element below the transition temperature to the austenite phase; the element is maintained at room temperature; the method includes grinding at least part of the element to a reduced diameter while flooding the element with cooling fluid to control the temperature of the element; the method includes controlling the grinding speed to control the temperature of the element; the temperature during grinding is below 300° F.; the temperature during grinding is room temperature; the method includes grinding the element to provide a taper; the method includes drawing the element to produce the reduced diameter portion; the method includes chemical etching of the element to produce the reduced diameter portion; the method includes applying to the element, a polymer coating; the method includes applying to the element, a lubricious coating; the method includes applying to the element, an antithrombogenic coating.

In yet another aspect, the invention features a guidewire device comprising, in at least its distal portion, an element consisting of a metal alloy having the elemental composition of a superelastic alloy and at room temperature to body temperature a substantially linear stress strain curve exhibiting a yield point without passing through a substantial plateau. The distal portion of the guidewire is deformable beyond the yield point to a desired set shape.

Preferably, the alloy is selected from In—Tl, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn.

In another aspect the invention features a method of forming a guidewire device by providing an element comprised of an alloy having the composition of a superelastic alloy and at room to body temperature having a linear stress-strain curve exhibiting a yield point without passing through a substantial plateau, the element having initial properties of elasticity and straightness and reducing the diameter of at least a portion of the guidewire under conditions to maintain the initial properties. Thereafter, the element is incorporated into a guidewire device, with the reduced diameter portion forming part of the distal portion of the guidewire device, the distal portion being elastically flexible while being capable of assuming a desired permanent set by application of manual stressing of the distal region beyond its yield point.

In various aspects, the method includes forming the element by cold drawing to impart the initial properties; the alloy is selected from In—Tl, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn.

These and other features and advantages will be seen from the following description of a presently preferred embodiment, and from the claims.

DESCRIPTION OF THE PREFERRED EMBODIMENT

We first briefly describe the drawings.

Drawings

FIGS. 5, 5a, 5b, and 5c illustrate the use of the guidewire of the invention.

FIG. 6 compares stress strain curves from various cores.

Figure 7:
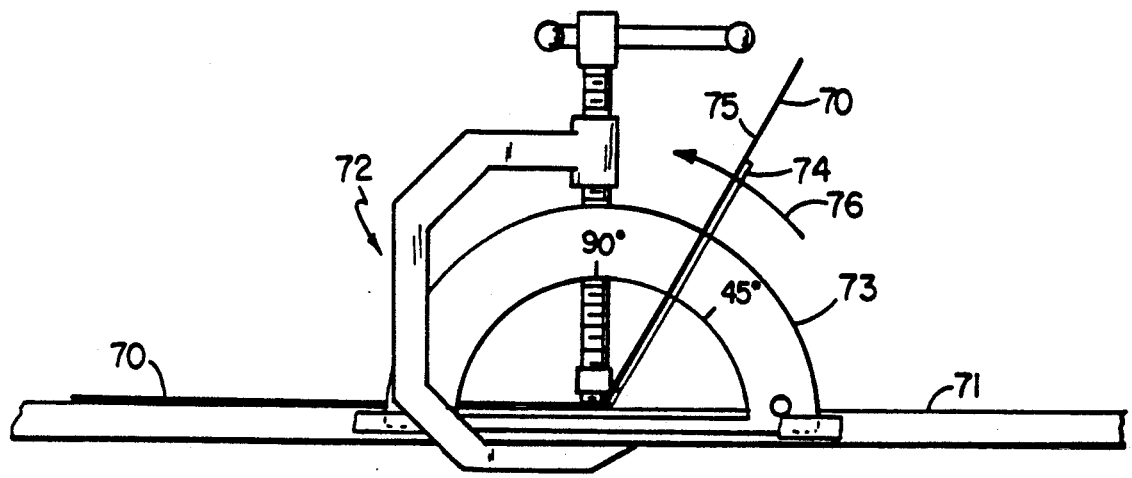

FIG. 7 illustrates the experimental apparatus used to obtain test results as described in Test Example 2.

Structure

Figure 1:
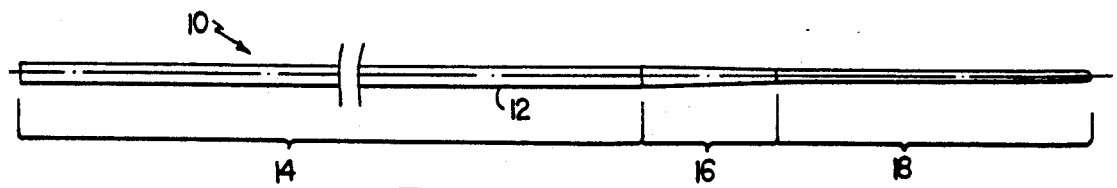
FIG. 1 is a plan view of the core of a guidewire of the invention.
Figure 2:
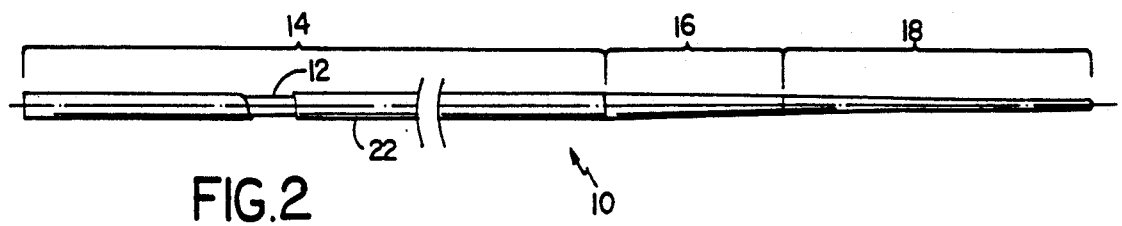
FIG. 2 is a plan view partially cutaway of a guidewire having a core as in FIG. 1 and including a polymer coating.
Figure 3:
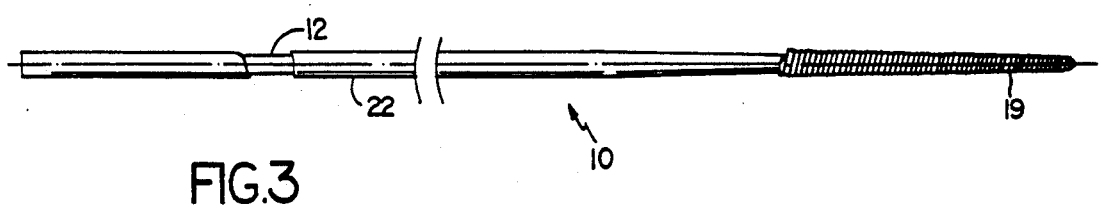
FIG. 3 is a plan view of a guidewire having a core as in FIG. 1 and including a distal element coil.

Referring to FIGS. 1 to 3, a guidewire 10 of the invention has an elongated core element 12 formed of a precursor of a superelastic alloy. The core 12 includes a proximal body section 14 of constant diameter, a taper 16 and a distal end 18 of constant, smaller diameter than the body section 14.

According to the invention, the core 12 is formed of a linear elastic precursor of a superelastic (or pseudoelastic) metal alloy. The guidewire core is manufactured from a raw element that is made of the precursor alloy. The raw element is made by repeatedly drawing ingots of the precursor alloy without the application of heat (cold drawing). The alloy precursors of superelastic alloys are in the martensite crystalline phase at room temperature to body temperature and are linear elastic materials, i.e., they are easily permanently bent (plastically deformed) upon reaching a given stress and strain, known as the yield point, without passing through a substantial plateau.

Raw elements formed of stress-induced superelastic materials, on the other hand, are formed by drawing an ingot of the precursor alloy while simultaneously heating. In the unstressed state at room temperature such superelastic materials occur in the austenite crystalline phase and upon application of stress, exhibit stress-induced austenite-martensite crystalline transformations which produce non-linear elastic behavior. As a result, superelastic materials are able to undergo repeated high strain deformations without plastic deformation. When the deforming stress is removed the strain is recovered and there is little or no permanent or plastic deformation.

It is an advantage of superelastic materials that, after imparting the superelastic properties by proper processing, they may be highly strained (deformed), yet still regain their original shape upon release of the deforming stress. It is an advantage of common linear elastic materials that they can be conveniently and easily plastically deformed to a desired shape with relatively little strain.

The present invention contemplates guidewires formed of certain special alloys that are highly elastic, i.e. have high strain prior to yield, although typically not as high as the maximum strain of superelastic materials, but are also easily plastically deformable. Such alloys are those that are precursors of superelastic alloys, i.e., they have the same chemical constituents as superelastic alloys, but have not been processed to impart the superelastic property.

Figure 4:
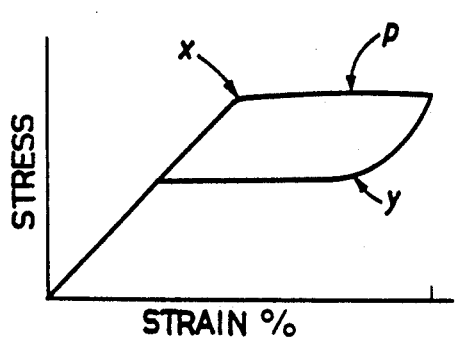
FIGS. 4 and 4a, illustrate idealized stress strain curves for superelastic (FIG. 4) and linear elastic (FIG. 4a) materials.
Figure 4A:
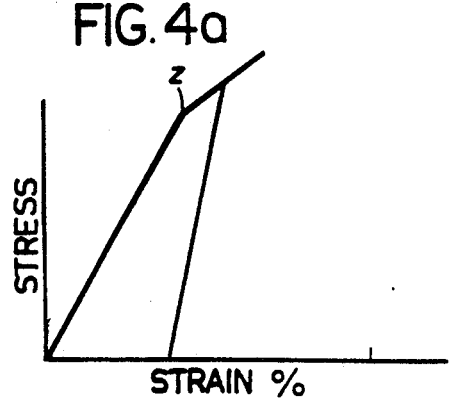

Referring to FIGS. 4 and 4a, schematic stress versus strain curves for a superelastic alloy (FIG. 4) and a super elastic precursor alloy that exhibits linear elastic properties (FIG. 4a) are compared. For a superelastic alloy, as stress is increased, the strain increases to a point (X) where the material undergoes a transformation from the austenite to the martensite phase. Thereafter, stress remains substantially constant while strain is increased, forming a constant stress plateau (P). The superelastic material is reversibly deformable. It returns to its original length on curve (Y) as the stress is released. This cycle may occur repeatedly, without appreciable change in dimension or plastic deformation.

In FIG. 4a, the schematic stress-strain curve for a superelastic precursor material having linear elastic properties is shown for comparison to FIG. 4. The strain in this case increases reversibly to the plastic yield point (Z) without passing through a substantial plateau. At and above the yield point, the material becomes plastically, irreversibly deformed. In the present invention, at least the taper 16 or distal end 18 of the core member 12 is a linear elastic material formed of the precursor alloy of a superelastic material.

A preferred precursor of a superelastic alloy is a nickel-titanium (55%/45%) system (available as Alloy Bu from Ray-Chem Corp., Menlo Park, Calif.). Precursors of other superelastic alloys may also be used. These include e.g., Silver-Cadmium (Ag—Cd), Gold-Cadmium (Au—Cd), Gold-Copper-Zinc (Cu—Au—Zn), Copper-Zinc (Cu—Zn), Copper-Zinc-aluminum (Cu—Zn—Al), Copper-Zinc-Tin (Cu—Zn—Sn), Copper-Zinc-Xenon (Cu—Zn—Xe), Iron Beryllium ($Fe_3Be$), Iron-Platinum ($Fe_3Pt$), Indium-Thallium (In—Tl), iron-maganese (Fe—Mn) Nickel-Titanium-Vanadium (Ni—Ti—V). Iron-Nickel-Titanium-Cobalt (Fe—Ni—Ti—Co) and Copper-Tin (Cu—Sn). See Schetsky, L. McDonald, "Shape Memory Alloys", *Encyclopedia of Chemical Technology* (3rd ed.), John Wiley & Sons, 1982, vol. 20, pp. 726–736 for a full discussion of superelastic alloys.

Referring back to FIGS. 1 to 3, in one embodiment for use in angiography, core element 12, is typically about 145 cm long or about 450 cm long for a GI wire, has a body portion 14 of, e.g., about 0.020 to 0.029 inch diameter, and a tip portion 18, e.g., about 0.007 inch diameter that is about 2 to 10 cm long, with a smoothly tapering portion 16, e.g., about 7 to 10 cm long, all formed of a superelastic precursor alloy. The tapered portion of the wire 12 could also be continuous (not shown) rather than stepped as recited herein above. Body portion 14 of the core forms a generally stiffer region for torque transmission while the end section 18 and the tapering portion 16 at the distal end of the guidewire are of relatively greater flexibility due entirely to the reduced diameter.

Referring now to FIG. 2, the guidewire may include a polymer coating 22, e.g., polytetrafluoroethylene, Teflon ®, disposed over the core 12 to facilitate smooth motion through body lumens. Other embodiments might include a lubricious coating as described, for example, by Terumo in EP application 85 106929.4, filed Jun. 4, 1985. Another lubricious coating is described in U.S. Pat. No. 5,091,205 (issued continuation in part of U.S. application Ser. No. 297,331, filed Jan. 31, 1989, the entire contents of which are incorporated herein by reference). An antithrombogenic coating may also be applied. A coating which is both lubricious and includes heparin is described in allowed copending application, entitled: "Lubricious Antithrombogenic Catheters, Guidewires and Coatings" Ser. No. 07/451,507 by Ronald Sahatjian and Kurt Amplatz filed Dec. 15, 1989, the entire contents of which is also incorporated herein by reference.

Referring now to FIG. 3, a spring coil member 19 may also extend over a portion, such as the distal tip, of the core. The spring coil aids in transmission of torque to the distal end when manipulating the proximal portion to navigate tortous lumens. Preferably, the coil is highly flexible, more flexible than the core, so that the coil may easily conform to the shape of the core when curvature is imparted by the physician. A radiopaque platinum coil is also preferable since it can facilitate observing and positioning of the element using radioscopic means. A method for fixing platinum coils to superelastic alloys is discussed in allowed commonly owned copending application Ser. No. 07/644,671 filed Jan. 18, 1991, continuation of 374,348, filed Jun. 28, 1989, which is also hereby incorporated by reference. Such methods as described therein can also be used with precursor alloys.

It will also be understood that the precursor material could be used for just the tip or taper of the guidewire.

Use

Referring to FIGS. 5–5c, guidewire 10 can be used, for example, for treatment of vascular ailments. Generally, a physician inserts the distal end of guidewire 10 into a body lumen 56 such as a blood vessel. Just prior to entry into the body for locating the tip at, for example, the point of an occlusion 50 (FIGS. 5b–5c), the distal tip may be preformed manually by the physician (FIGS. 5–5a) according to his judgment as to the degree and nature of curvature best for the situation. In FIGS. 5–5a, the guidewire 10, may be taken from sterile storage and the physician using his hands 52, 53, can grasp the end and shape the end to have the desired curvature 54 that complements the curvature of a lumen.

The guidewire 10 for angioplasty is inserted using, for example, the Seldinger technique, through an introducer sheath 59, placed in a limb 60, like the leg, to give access to the lumen 56 such as the femoral artery. Axial thrust (arrow A) is applied to the proximal portion to advance the guidewire 10 (FIG. 5b) in the lumen. In the example illustrated in the FIGS. 5–5c, the curved end 54 of guidewire 10 is advanced through e.g, a large body lumen 56 to the desired position near a vessel 58, and steered by rotating body portion 14 (arrow R) to direct curved end 54 to the vessel 58 (FIG. 5c). (A G.I. guidewire may be introduced through an endoscope, (not shown), for gastrointestinal procedures, with benefits similar to the above identified angioplasty procedure). A catheter can then be advanced over guidewire 10, and the guidewire removed when catheter is in place. Because of the high flexibility and elongation of the precursor of a superelastic alloy, the guidewire can negotiate highly tortuous passageways. Because the material is linearly elastic and deformable, the guidewire can be deformed by the physician just prior to entry for optimum shaping for ease of steering the element into a desired curved lumen.

Manufacture

The guidewires of the present invention are formed of a precursor of a superelastic alloy. Guidewires that are substantially straight and capable of high elastic strain are manufactured from raw superelastic precursor element by taking care to prevent heating of the precursor that would result in heat treatment. In the event that excessive heating occurs, when the material is subsequently cooled, the straightness of the element may be lost. It also appears that in some cases the element becomes limp and less springy.

The precursor alloys, when first cold drawn from ingots into raw elements of constant diameter occur in the martensite phase at room temperature (as opposed to the superelastic alloy themselves which are drawn while heating and occur in the austenite phase at room temperature). The springiness and straightness in the martensite precursors we believe is a result of the cold drawing process which gives the martensite crystalline structure a preferred orientation. The high strain and straightness of the material can be maintained as long as the material is not substantially heated. When excessively heated, the materials pass through a transition to the austenite phase and, after cooling and returning to the martensite phase, the crystalline orientation or work hardening of the martensite which was imparted during the initial cold drawing is lost, leading to a less straight, and sometimes somewhat less spring material.

The temperature of the raw precursor element is kept below, preferably well below, (e.g., room temperature,) the transition temperature from martensite to austenite during processing of the precursor material when forming guidewires. For the Ni—Ti alloy (Alloy Bu) of the preferred embodiment, the transition temperature is approximately 300° F.

For forming a tapered guidewire, a tapering machine which renders a tapered section by center-less grinding with a friction wheel may be used. Such apparatus are available, for example, from Royal Master Corp, Oakland, N.J. (models TG-12x3 (stepless) or TG-12x4). The friction of the grinding wheel against the alloy can lead to a rise of temperature of the material. To counter this, the rotation of the wheel, and the volume of liquid coolant flowing about the wheel and tip must be controlled. For example, on a Royal Master model TG-12x4, the rotation is reduced from a typical speed of about 40-50 rpm to about 19 rpm. The flow of room temperature coolant is typically half the maximum permitted by the model TG-12x4. Under these conditions, the tip may be ground to a taper without significantly increasing the temperature. It will be understood that various operating conditions might be adjusted and controlled to maintain a low temperature during the tapering step. For example, the temperature of the coolant might be reduced or its flow increased.

Other tapering methods could also be used, and the temperature of the grinding region controlled. For example, it also is known to form tapers by chemical etching or by drawing on an end or both ends of a element.

TEST EXAMPLES

Example 1

Referring now to FIG. 6, stress-strain curves from a stress testing machine for superelastic (curve A), superelastic precursor material (curve B) and a stainless steel element (curve C) are shown. The curves measure stress as a function of the percentage of strain for element pieces while drawing an end of the element. Stress testing machines are available from Instron Corp., Canton, Mass. In FIG. 6, the percent strain is shown along the ordinate and measured stress along the abscissa.

In FIG. 6, curve A, the data shown is for a superelastic guidewire (Ni—Ti Alloy—BB, from Raychem Corp.) of about 0.020 inch outer diameter, Instron jaw separation 4 inches, speed 20 inches/min. The strain initially increases substantially linearly with stress up to point (x) at which point, the material transforms from austenite to martensite and stress is relatively constant with increasing strain, plateau (P). (The path y as in FIG. 4 is not shown since the Instron machine was operated to increase stress until the material failed by pulling apart at point (w)).

In FIG. 6, curve B, the Instron machine data shown is for a guidewire (0.020 inch) made from a linear elastic precursor (Alloy Bu) of the superelastic alloy tested in FIG. 6. In FIG. 6, curve C, the data for a stainless steel guidewire (0.020 inch) is shown. Both the linear elastic precursor and the stainless steel guidewires show no stress strain plateau indicating a phase change.

In the tests illustrated in FIG. 6, the strain before yield (plastic deformation) increased in order from stainless steel, to precursor, to superelastic.

Example 2

In table I, the bending angle at the yield point of a guidewire tip for stainless steel, a linear elastic precursor of a superelastic material and a superelastic material are given. Using the apparatus shown in FIG. 7, the elements were tested to determine the point of plastic deformation. A sample of element 70 was secured to a table 71 using a C-clamp 72. A protactor 73 was used to measure the angle. Using a steel ruler 74 a portion 75 of the element sample was moved in the direction of the arrow 76 until plastic deformation was observed. The diameter of the elements is given in inches in table I.

TABLE I

| | Bending Angle at the Yield Point | | |
|---|---|---|---|
| | Material | Diameter | Angle at Yield |
| Stainless Steel (Linear Elastic) | Stainless Steel | 0.0230 | 35° |
| Precursor of a Superelastic Alloy (Linear Elastic) | Alloy Bu | 0.0234 | 80° |
| Superelastic Alloy | Alloy BB | 0.0235 | 150° |

The stainless element easily takes a set and yields permanently at the 35° angle, whereas both the precursor of the superelastic and the superelastic were observed to take on only a very slight kink, taken to be an artifact of the test, at a first angle point (55° for precursor alloy and 60° for superelastic alloy BB). After this there occurred a broad range in arc (55°-80° for the precursor; 60°-150° for the superelastic) through which there was no additional change in permanent deformation until reaching the upper angle number shown in the table. At this point, significant permanent deformation is imparted to the elements.

Other embodiments are within the following claims.

What is claimed is:

1. A guidewire device having a distal portion comprised of a precursor of a superelastic alloy, said precursor portion exhibiting no phase transition in response to deforming stress and having a linear stress-strain curve extending to a yield point without passing through a substantial plateau in which stress remains substantially constant while strain is varied, the distal precursor portion of said guidewire being deformable beyond said yield point to a desired set shape.

2. The guidewire device of claim 1 wherein said precursor is selected from the group consisting of an alloy of In—Tl, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn.

3. The guidewire of claim 2 wherein said alloy is selected from the group consisting of Ni—Ti, Cu—Al—Ni and Cu—Zn—Al.

4. The guidewire of claim 1 wherein said precursor is an alloy of about 55%/45% Ni—Ti.

5. The guidewire device of claim 1 in which at least part of said distal portion is smaller than an integral portion of said guidewire proximal thereto, which is also comprised of said precursor of a superelastic alloy.

6. The guidewire device of claim 5 in which at least part of the guidewire formed of said precursor of a superelastic alloy is tapered from a larger to a smaller size in the direction of the distal end of said guidewire.

7. The guidewire of claim 5 in the form of an angiographic guidewire having a total length of about 145 cm, a body portion of about 0.020 to 0.290 inch diameter, a taper portion about 7 to 10 cm long and a tip portion about 2 to 10 cm long with a diameter of about 0.007 inch, said body portion, taper portion and tip portion comprised of said precursor of a superelastic alloy.

8. The guidewire of claim 5 in the form of a gastrointestinal guidewire having a total length of about 450 cm, a body portion of about 0.020 to 0.290 inch diameter, a taper portion about 7 to 10 cm long and a tip portion about 2 to 10 cm long with a diameter of about 0.007 inch, said body portion, taper portion and tip portion comprised of said precursor of a superelastic alloy.

9. The guidewire of claim 6 wherein there is a portion of said guidewire distal to said taper, said portion having diameter no greater than the diameter of the most distal portion of said taper.

10. The guidewire of claim 6 wherein the distal portion of said guidewire continuously tapers distally to the smallest diameter at the distal end of the guidewire.

11. The guidewire device of claim 1 having a core element comprised of said precursor, said core element extending proximally, integrally from said distal portion.

12. The guidewire of claim 1 further comprising a polymeric external coating.

13. The guidewire of claim 12 wherein said coating is polytetrafluoroethylene.

14. The guidewire of claim 12 wherein said coating is a lubricious polymer.

15. The guidewire of claim 12 or 14 wherein said coating includes an antithrombogenic agent.

16. The guidewire of claim 14 wherein said agent is heparin.

17. The guidewire of claim 1 wherein said distal portion comprises an element comprised of said precursor of a superelastic alloy and further including a flexible spring coil surrounding said element.

18. The guidewire of claim 17 wherein said spring coil is more flexible than said element.

19. A guidewire device having a distal portion comprised of a precursor of a superelastic alloy, selected from the group consisting of an alloy of In—Tl, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn, said precursor portion exhibiting no phase transition in response to deforming stress and having a linear stress-strain curve extending to a yield point without passing through a substantial plateau in which stress remains substantially constant while strain is varied, the distal precursor portion of said guidewire being deformable beyond said yield point to a desired set shape, where at least part of the guidewire formed of said precursor of a superelastic alloy is tapered from a larger to a smaller size in the direction of the distal end of said guidewire where the tip of said guidewire is no larger than the most distal portion of said taper.

20. The guidewire of claim 19 wherein there is a portion of said guidewire distal to said taper, said portion having diameter no greater than the diameter of the most distal portion of said taper.

21. The guidewire of claim 19 wherein the distal portion of said guidewire continuously tapers distally to the smallest diameter at the distal end of the guidewire.

22. The guidewire of any one of claims 19 or 21 wherein said precursor is an alloy of about 55%45% Ni—Ti.

23. A guidewire device having a distal portion comprised of a Ni—Ti alloy, said portion exhibiting no phase transition in response to deforming stress and having a substantially linear stress-strain curve extending to a yield point without passing through a substantial plateau in which stress remains substantially constant while strain is varied, the distal portion of said guidewire being deformable beyond said yield point to a desired set shape.

24. The guidewire of claim 23 wherein said alloy is about 55%/45% Ni—Ti.

25. A guidewire device having a distal portion comprised of a Ni—Ti alloy in the martensite phase, said portion exhibiting no phase transition in response to deforming stress and having a substantially linear stress-strain curve extending to a yield point without passing through a substantial plateau in which stress remains substantially constant while strain is varied, the distal portion of said guidewire being deformable beyond said yield point to a desired set shape.

26. The guidewire device of claim 25 in which at least part of said distal portion is smaller than an integral portion of said guidewire proximal thereof.

27. The guidewire of claim 25 or 26 wherein said alloy is about 55%/45% Ni—Ti.

* * * * *

UNITED STATES PATENT AND TRADEMARK OFFICE
CERTIFICATE OF CORRECTION

PATENT NO. : 5,238,004
DATED : August 24, 1993
INVENTOR(S) : Ronald Sahatjian, Fernando Alvarez de Toledo It is certified that error appears in the above-indentified patent and that said Letters Patent is hereby corrected as shown below:

On the title page: Item [56]

Under FOREIGN PATENT DOCUMENTS, please insert the following:

| | | |
|---|---|---|
| 1435797 | 5/1976 | United Kingdom |
| 0113186 | 7/1984 | European Pat. Off. |
| 0340304 | 11/1989 | European Pat. Off. |
| 831575 | 5/1983 | World Int. Prop. O. |
| 0166998 | 1/1986 | European Pat. Off. |

Signed and Sealed this

Sixteenth Day of August, 1994

Attest:

BRUCE LEHMAN

Attesting Officer     Commissioner of Patents and Trademarks